US011814946B2

United States Patent
Jandhyala et al.

(10) Patent No.: US 11,814,946 B2
(45) Date of Patent: Nov. 14, 2023

(54) EVALUATING ANNULAR MATERIAL IN A WELLBORE USING TRANSIENT THERMAL RESPONSE DATA

(71) Applicant: Halliburton Energy Services, Inc., Houston, TX (US)

(72) Inventors: Siva Rama Krishna Jandhyala, Katy, TX (US); John Paul Bir Singh, Kingwood, TX (US); Krishna Babu Yerubandi, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 19 days.

(21) Appl. No.: 17/573,236

(22) Filed: Jan. 11, 2022

(65) Prior Publication Data

US 2023/0220763 A1 Jul. 13, 2023

(51) Int. Cl.
*E21B 47/005* (2012.01)
*E21B 33/138* (2006.01)
*E21B 47/07* (2012.01)
*G01N 25/72* (2006.01)
*G01N 33/38* (2006.01)

(52) U.S. Cl.
CPC .......... *E21B 47/005* (2020.05); *E21B 33/138* (2013.01); *E21B 47/07* (2020.05); *G01N 25/72* (2013.01); *G01N 33/383* (2013.01); *E21B 2200/20* (2020.05)

(58) Field of Classification Search
CPC ...... E21B 47/005; E21B 33/138; E21B 47/07; E21B 2200/20; E21B 33/00; G01N 33/383
See application file for complete search history.

(56) References Cited

U.S. PATENT DOCUMENTS

| 8,230,915 | B2 | 7/2012 | Weng | |
| 8,305,228 | B2* | 11/2012 | Vigneaux | E21B 33/16 340/854.6 |
| 8,453,760 | B2 | 6/2013 | Fincher et al. | |
| 8,961,006 | B2* | 2/2015 | Gleitman | E21B 47/07 374/161 |

(Continued)

OTHER PUBLICATIONS

Unpublished U.S. Appl. No. 17/039,054, filed Sep. 30, 2020—stored in USPTO Image File Wrapper System, in accordance with the Waiver of the Copy Requirements in 37 CFR 1.98 for cited pending U.S. Patent applications, 1287 O.G. 163 (Oct. 19, 2004).

(Continued)

*Primary Examiner* — Catherine Loikith
(74) *Attorney, Agent, or Firm* — Kilpatrick Townsend & Stockton LLP

(57) ABSTRACT

A method for identifying zones in an annulus with poor cementing that may include deploying a fiber optic cable within the wellbore, creating a temperature gradient in the wellbore, and collecting temperature data over a period of time as the wellbore returns to a thermal equilibrium. The method may also include comparing the temperature data collected by the fiber optic cable at one or more locations to predicted temperature data over the period of time at the one or more locations to identify locations where the measured temperature data deviates from the predicted temperature data for identifying locations or zones of the annulus that have poor cementing.

20 Claims, 6 Drawing Sheets

(56) References Cited

U.S. PATENT DOCUMENTS

| | | | | |
|---|---|---|---|---|
| 9,835,022 B2 * | 12/2017 | Quintero | ................. | E21B 47/07 |
| 10,125,602 B2 * | 11/2018 | Al-Hussain | ............. | E21B 47/10 |
| 2015/0126929 A1 | 5/2015 | Franklin et al. | | |
| 2019/0264555 A1 | 8/2019 | Seabrook et al. | | |
| 2021/0238985 A1 | 8/2021 | Yerubandi et al. | | |

OTHER PUBLICATIONS

Unpublished U.S. Appl. No. 17/071,839, filed Oct. 15, 2020—stored in USPTO Image File Wrapper, in accordance with the Waiver of the Copy Requirements in 37 CFR 1.98 for cited pending U.S. Patent applications, 1287 O.G. 163 (Oct. 19, 2004).

Corre et al., "Numerical Computation of Temperature Distribution in a Wellbore While Drilling", (SPE-13208) Paper presented at the SPE Annual Technical Conference and Exhibition, Houston, Texas, Sep. 1984, 12 pages.

Hasan, "Aspects of Wellbore Heat Transfer During Two-Phase Flow", (SPE-22948) Prod & Fac 9. doi: https://doi.org/10.2118/22948-PA, 1994, 9 pages.

Marshall et al., "A Computer Model to Determine the Temperature Distributions in a Wellbore", J Can Pet Technol 21, 1982, 13 pages.

International Search Report and Written Opinion, PCT/US2022/051516, dated Apr. 12, 2023, 11 pages.

* cited by examiner

EVALUATING ANNULAR MATERIAL IN A WELLBORE USING TRANSIENT THERMAL RESPONSE DATA

TECHNICAL FIELD

The present disclosure relates generally to wellbore construction operations and, more particularly (although not necessarily exclusively), to evaluating annular material in a wellbore using transient thermal response data.

BACKGROUND

A wellbore can be a hole drilled into a subterranean rock formation. The wellbore can include an annulus that can be a space between a wall of the wellbore and a casing string that may be run through the wellbore. A cementing material can be used to seal the annulus and can provide the wellbore with structural integrity and can prevent undesirable flow paths that can allow fluids in one region of the wellbore to mix with fluids in another region of the wellbore.

DETAILED DESCRIPTION

Figure 1:
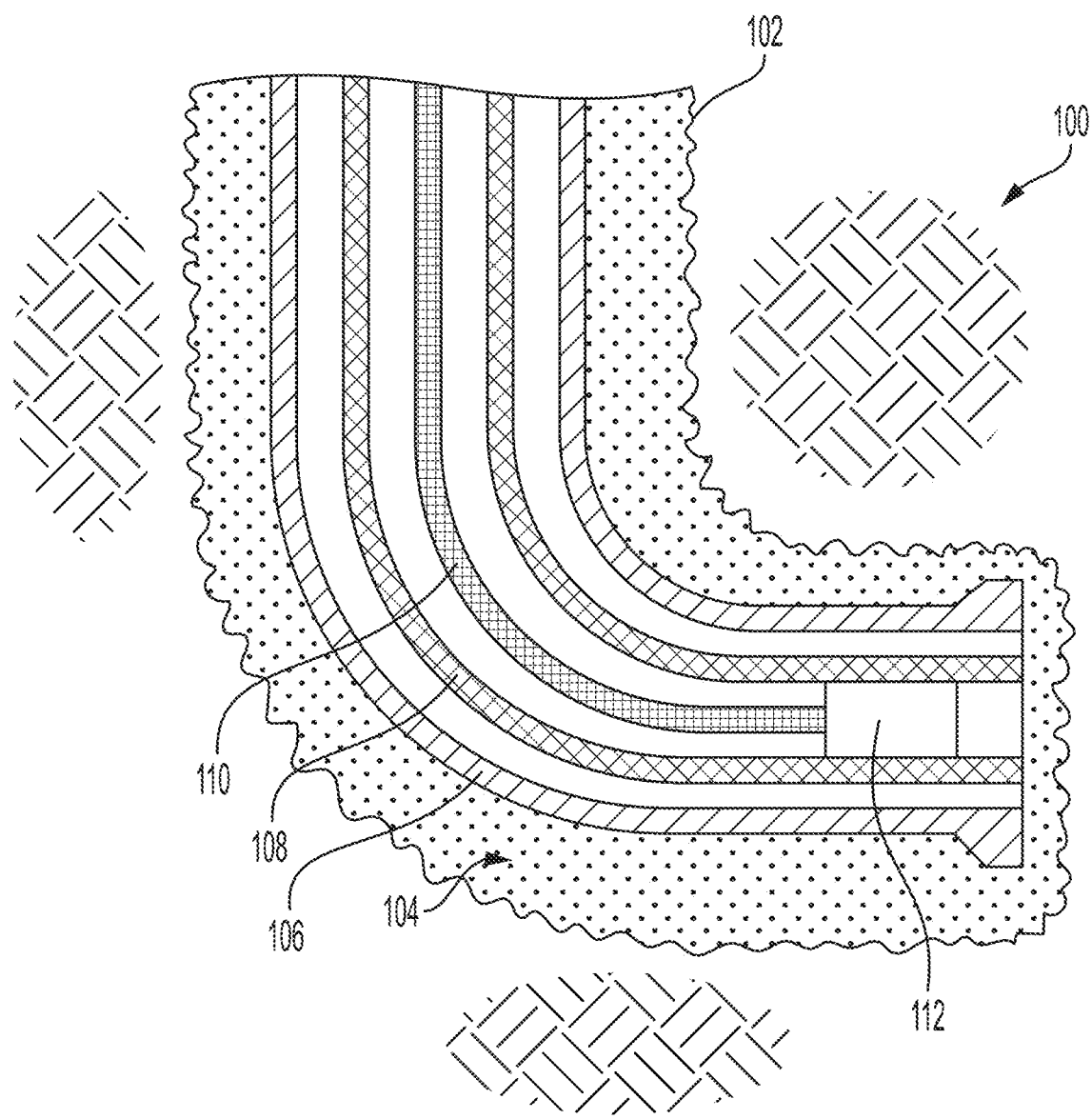
FIG. 1 is a cross-sectional diagram of a well system including a downhole tool positioned within a wellbore according to one example of the present disclosure.

Certain aspects and examples of the present disclosure relate to evaluating an annular material in an annulus of a wellbore using transient thermal response data. The annular material can be a material, such as cement, that can be used to seal the annulus of the wellbore and can provide the wellbore with structural integrity and can prevent fluids in one region of the annulus from mixing with fluids in another region of the annulus. Poor zonal isolation, resulting in flow through the annulus is undesirable after a cement is placed and set in the annulus. Such poor zonal isolation can occur due to inadequate placement practices during cementing or as a result of long term damage during well operations. Damage to the cement in the annulus can be remedied by perforating the casing string and using techniques such as squeeze cementing. Well systems and methods described herein can utilize transient thermal response monitoring to identify locations in the annulus that are not well cemented and may require repair.

According to examples of the present disclosure, a sensor, for example a fiber optic cable, can be positioned downhole for collecting data regarding temperature along the length of the wellbore. The data can be collected as a function of time. A fluid may be circulated through the wellbore in sufficient quantity, at a sufficient temperature, and for a sufficient amount of time to provide for a sufficient temperature gradient in the wellbore in a radial and/or axial direction, and in some aspects in both a radial and an axial direction. Upon ceasing circulation of the fluid the temperature along the length of the wellbore as measured by the fiber optic cable can be monitored over a period of time. The temperature data collected over the period of time along the length of the wellbore can correspond to transient thermal response data generated as a response to the disruption of the thermal equilibrium in the wellbore by the circulated fluid. The transient thermal response can occur as a result of conduction and convection processes that occur within the wellbore, and can depend on the material around the wellbore, including in particular the material in the annulus between the casing string and the wellbore. The temperature at points along the length wellbore can be measured over a period of time and that transient thermal response data can be used to identify zones of the annulus with poor cementing.

The temperature data collected for a particular location or depth along the wellbore over a period of time (hereinafter "transient thermal response data") may be compared to a predicted transient thermal response for that location. The predicted transient thermal response can be determined using a mathematical model based at least in part on the conduction and natural convection process that occur in a wellbore having annular material of good cement. Zones or regions along the length of the wellbore that have transient thermal response data that deviates from the predicted response can correspond to zones or regions that are not well cemented. In some embodiments, the transient thermal response data may be used to determine the annular material in a zone where the measured data deviates from the predicted values. The annular material may be determined using the mathematical model and tuning or altering the input values in the model, including but not limited to the thermal properties of various material in the wellbore, (e.g cement, fluids, mud, etc.) to arrive at the observed transient thermal response data.

In some embodiments, upon identifying regions of a poor cement in the annulus that may result in undesirable flow paths, the regions may then be corrected using cementing techniques such as squeeze cementing. While sonic and acoustic data can be used to collect data regarding an annular material, a signal in sonic or acoustic data can be difficult to distinguish from noise in examples where a density of the annular material is similar to a density of a fluid in the wellbore. Sonic and acoustic techniques may also result in a limited radial resolution when evaluating cement behind multiple casing strings. Transient thermal response data can be acquired by the fiber optic cable regardless of the relative density of the annular material and can result in data that is easier to interpret and is more reliable. Transient thermal response data can be used to determine a state of the annular material where the fiber optic cable is separated from the annular material by a single casing string, or in some examples by multiple casing strings. Using transient thermal response data can be relatively inexpensive and may be logistically simple.

Illustrative examples are given to introduce the reader to the general subject matter discussed herein and are not intended to limit the scope of the disclosed concepts. The following sections describe various additional features and examples with reference to the drawings in which like numerals indicate like elements, and directional descriptions are used to describe the illustrative aspects, but, like the illustrative aspects, should not be used to limit the present disclosure.

FIG. 1 is a cross-sectional diagram of a well system according to one example of the present disclosure. The wellbore 102 may be surrounded by a subterranean rock formation 100. The wellbore 102 may include a casing string 106. The casing string 106 can be an assembled length of pipe that can be run into a wellbore 102. The casing string 106 can be encapsulated by an annular material 104 in the annulus between the casing string 106 and the wellbore 102. In some cases, the annular material 104 may be cement. In some examples a tubing 108 may extend through the casing string 106. The tubing 108 can allow for a circulation of fluid in a wellbore by providing a path for the fluid to flow. A landing device 112 can be deployed downhole in the wellbore 102 within the tubing 108. A thermal sensor, shown in FIG. 1 as a fiber optic cable 110, can extend along a length of the wellbore 102 and may collect data regarding the temperature at points along the length of the wellbore 102 over a period of time. The fiber optic cable 110 may be coupled to the landing device 112. In some embodiments one or more different thermal sensors may be used other than the fiber optic cable 110. The data collected by the fiber optic cable 110 may be transmitted to a computing device at a surface of the wellbore 102. The temperature data collected along the length of the wellbore over a period of time, as described further below, may be used to identify zones where the annular material 104 is not well cemented, according to embodiments of the present disclosure. Though the fiber optic cable 110 is depicted as positioned within the tubing 108 it may be positioned in other locations within the wellbore in other embodiments, including but not limited to within the annulus between the casing string 106 and the wellbore 102, inside the casing string 106, or in any other suitable location in thermal proximately to the fluid circulated within the wellbore.

Figure 2:
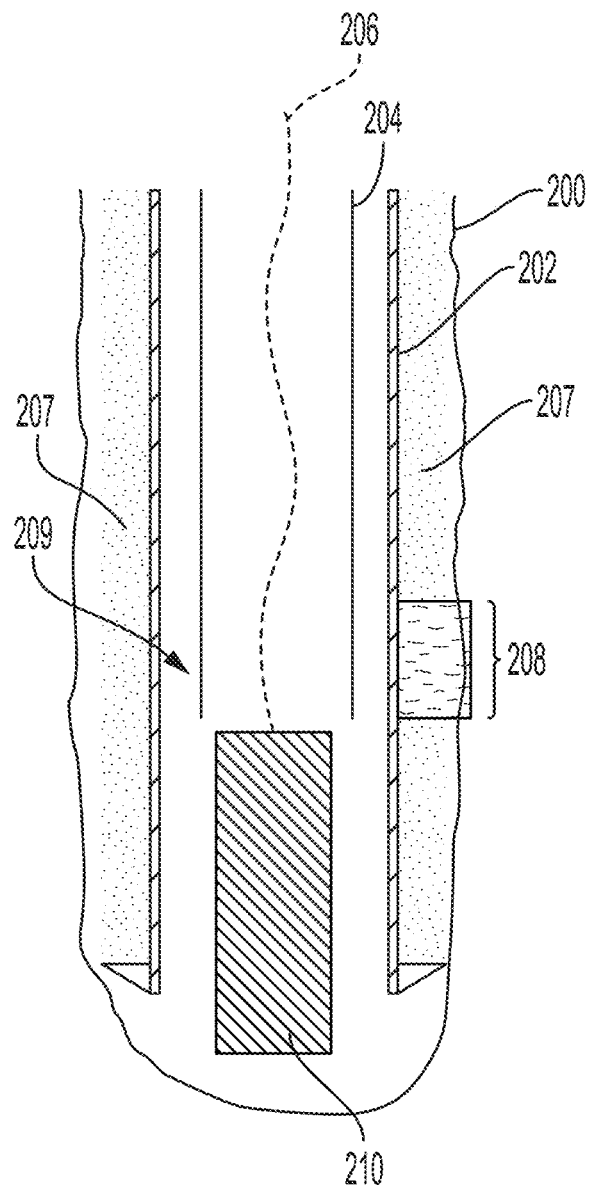
FIG. 2 is a cross-sectional schematic diagram a downhole tool positioned within a wellbore for evaluating an annular material positioned downhole according to one example of the present disclosure.

FIG. 2 is a cross-sectional schematic diagram a downhole tool positioned within a wellbore for evaluating an annular material positioned downhole according to one example of the present disclosure. The wellbore 200 may be surrounded by a subterranean rock formation (not depicted). A casing string 202 may be positioned within the wellbore 200. The casing string 202 can be an assembled length of pipe that can be run into a wellbore 200. The casing string 202 can be secured in place by an annular material 207 in an annulus between an outer surface of the casing string 202 and the wellbore 200. In some cases, the annular material 207 may be cement. In some examples a tubing 204 may be positioned downhole within the casing string 202. As shown and described in FIG. 3, a fluid 212 (fluid path shown by arrows) may be pumped downhole and circulated through wellbore within the tubing 204. The thermal properties of the fluid 212 may be known. A landing device 210 may be deployed downhole in the tubing 204. The landing device 210 may be coupled to a fiber optic cable 206 to help retain the fiber optic cable 206 in place downhole. The fiber optic cable 206 may act as a temperature sensor and may collect temperature data at various points along the length of the fiber optic cable 206 (corresponding to the length of the wellbore 200) over a period of time. The fiber optic cable 206 may transmit that data to a computing device at the surface. The fiber optic cable 206 may be deployed in a fiber-on-a-bobbin tool. The fiber-on-a-bobbin may include the fiber optic cable 206 coupled to grooves on a spool or bobbin that may be on the surface or attached to a plug (e.g. the landing device 210) and deployed downhole. The bobbin, if it is deployed on the surface, may be rotated to cause the fiber optic cable 206 to be reeled out and pushed into the wellbore. Alternatively, if the bobbin is attached to the plug, the fiber optic cable 206 can be reeled into the wellbore.

Figure 3:
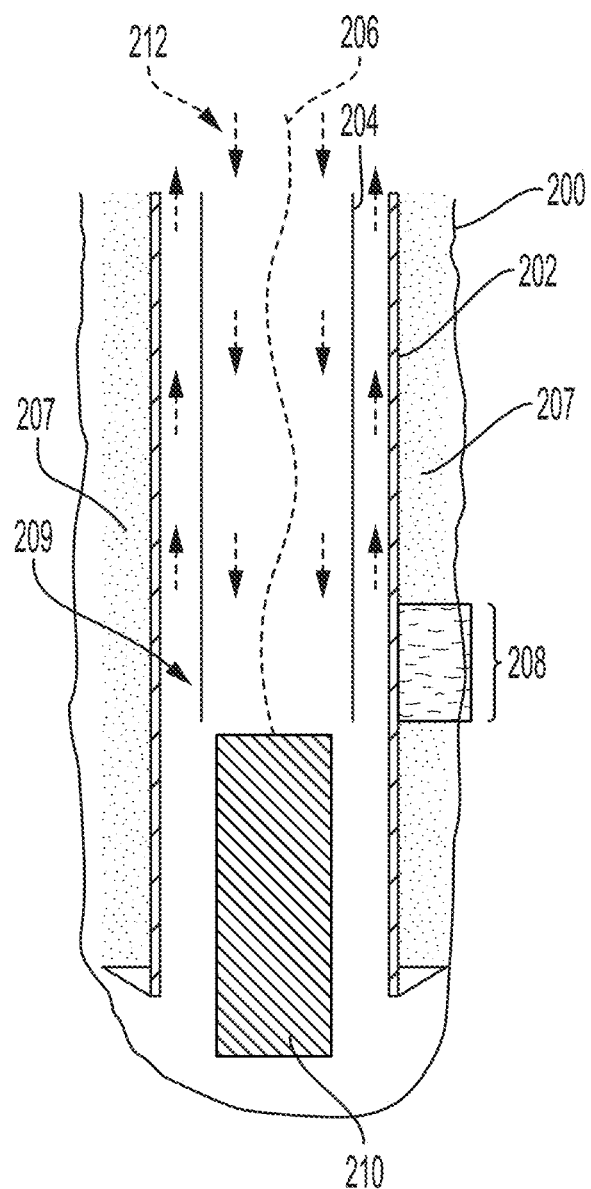
FIG. 3 is a cross-sectional schematic diagram of the downhole tool positioned within the wellbore of FIG. 2 as fluid is circulated within the wellbore for evaluating an annular material according to one example of the present disclosure.

Once the fiber optic cable 206 has been positioned downhole a fluid 212 may be pumped into the tubing 204 and circulated back through a second annulus 209 between the tubing 204 and the casing string 202, as shown in FIG. 3. Prior to circulating the fluid 212 in the wellbore 200, the wellbore 200 may be at thermal equilibrium. The temperature of the fluid 212 may be selected such that it is sufficiently higher or sufficiently lower than the temperature at the surface of the wellbore 200 so as to create a temperature gradient in the wellbore 200. For example, the difference between the temperature of the fluid 212 at the inlet may be between 50 and 100 degrees Celsius higher or lower than the temperature at the surface of the wellbore 200. For example, if the region of the wellbore 200 proximate the surface is cold, the temperature of the fluid 212 at the inlet may be 50-100 degrees Celsius higher than the temperature at the surface to create a sufficient temperature change along the length of the wellbore 200. In another example, if the region of the wellbore 200 proximate the surface is warm, the temperature of the fluid 212 at the inlet may be approximately 50-100 degrees Celsius lower than the temperature at the surface to create a sufficient temperature gradient. The temperature gradient can be calculated as a difference between the temperature of the fluid 212 at the inlet and the temperature of the surface of the wellbore 200. The fluid 212 may be circulated for approximately one to two hole volumes of the fluid 212, or any other sufficient amount or time. As the fluid 212 circulates the temperature along the length of the wellbore 200 as measured by the fiber optic cable 206 may change (i.e. increase or decrease) from the temperature prior to circulating the fluid 212. Thus, the circulation of the fluid 212 can disturb the temperature equilibrium along the length of the wellbore 200, for example within the production zone of the wellbore 200. The change in temperature in the wellbore 200 caused by the circulation of fluid 212 can be referenced as the temperature gradient in the wellbore 200 in both a radial direction and an axial direction.

As shown in FIG. 3, once the desired volume of the fluid 212 has been circulated in the wellbore 200, the fluid 212 may remain in the wellbore 200. Thereafter, for a desired period of time, the fiber optic cable 206 may collect temperature data at various points along the length of the wellbore 200. For example, the fiber optic cable 206 may collect data for about twenty minutes to about ninety minutes, about thirty minutes to about sixty minutes, about thirty minutes to about forty-five minutes, or any other suitable length of time. During that time, the data corresponding to the temperature at locations along the length of the wellbore 200 can correspond to transient thermal response data across depth and time in the wellbore 200. The temperature measured by the fiber optic cable 206 at a specific depth over a period of time can reflect the transient thermal response data at the specific depth. The transient thermal response data corresponding to locations, zones, or regions along the length of the wellbore 200 can be compared to a predicted transient thermal response to identify a region 208 where the annular material 207 positioned within the annulus between the casing string 202 and the wellbore 200 may be weak, damaged, or otherwise poorly cemented.

Figure 4:
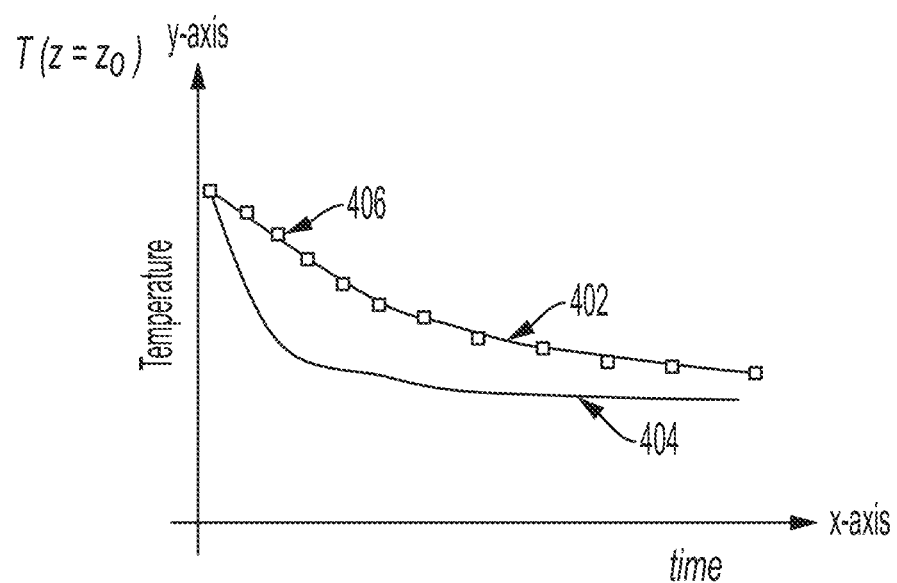
FIG. 4 is an exemplary graph of a temperature gradient that can be used to measure a transient thermal response on a fiber at a depth in a wellbore.

The exemplary, non-limiting, graph provided in FIG. 4 depicts a comparison of the temperature (depicted on the Y-axis) measured by the fiber optic cable 206 at a particular depth (shown as $z_o$) over a period of time (depicted on the X-axis) (i.e the transient thermal response data at $z_o$) for examples of good cement and poor cement at $z_o$. In an example depicted in FIG. 4, measured values of temperature as a function of time at $z_o$ are shown as points 406 and indicate a presence of good cement as the points 406 match predicted values of temperature as a function of time at $z_o$ for good cement that are shown as a line 402, rather than exemplary values of temperature as a function of time at $z_o$ for poor cement that are shown as line 404. The predicted transient thermal response can be determined using known mathematical models that rely at least in part on the known thermal properties of the well system materials (e.g., rock, cement, casing string, wellbore fluid, etc.). Therefore the predicted transient thermal response data can correspond to expectations for the temperature values over a period of time at location $z_o$ where proper cementing was assumed in the mathematical model. Where the measured transient thermal response data deviates from the predicted transient thermal response by at least a pre-determined amount, the respective location (or region or zone) may be identified as requiring repair due to poor cementing or other issues in the annulus between the casing string 202 and the wellbore 200.

In some aspects, the annular material of the region 208 where the transient thermal response data deviates from the predicted response may be identified using a mathematical model, for example the mathematical model used to determine the predicted transient thermal response. For example, the deviation between the measured and expected transient thermal response can be explained by tuning the thermal properties of the annular material in that zone using the mathematical model, as described further below with respect to FIG. 5.

In some embodiments, for example where the formation comprises the same or substantially the same material along the length of a the wellbore 200 or along a length of a zone or region of interest (e.g. the production zone) the transient thermal response data collected by the fiber optic cable 206 at a particular location may be compared to the transient thermal response data collected a different location along the wellbore 200 believed to have the same formation material. Deviations in the transient thermal response data between various points along the length of the wellbore 200 or the zone of interest may correspond to regions of poor cementing in the annulus between the casing string 202 and the wellbore 200. In other words, a self-consistent data analysis of the transient thermal response data may identify an anomalous locations along the wellbore 200 that may correspond to locations having poor cementing in the annulus. In some aspects, combining the data analysis of the transient thermal response data with other available information related to the history of the wellbore 200, the geometry of the wellbore 200, experience with previous wells in the region, and knowledge about a formation state of the wellbore 200 may further provide for comparing data along the length of the wellbore 200 for identifying locations or zones or regions where the annular material 207 positioned within the annulus between the casing string 202 and the wellbore 200 may be weak, damaged, or otherwise poorly cemented.

Once identified, a region of poor cement can be remediated by remedial cementing techniques, such as squeeze cementing. In some examples, squeeze cementing can involve applying pressure to a cement slurry or other treatment fluid into an undesired flow path, such as in the casing string 202 or the annulus. This can cause the cement to seal off the undesired flow path. The annular material 207 at the remediated location may, in some embodiments, be rechecked using the techniques and methods described above, after remediation.

Figure 5:
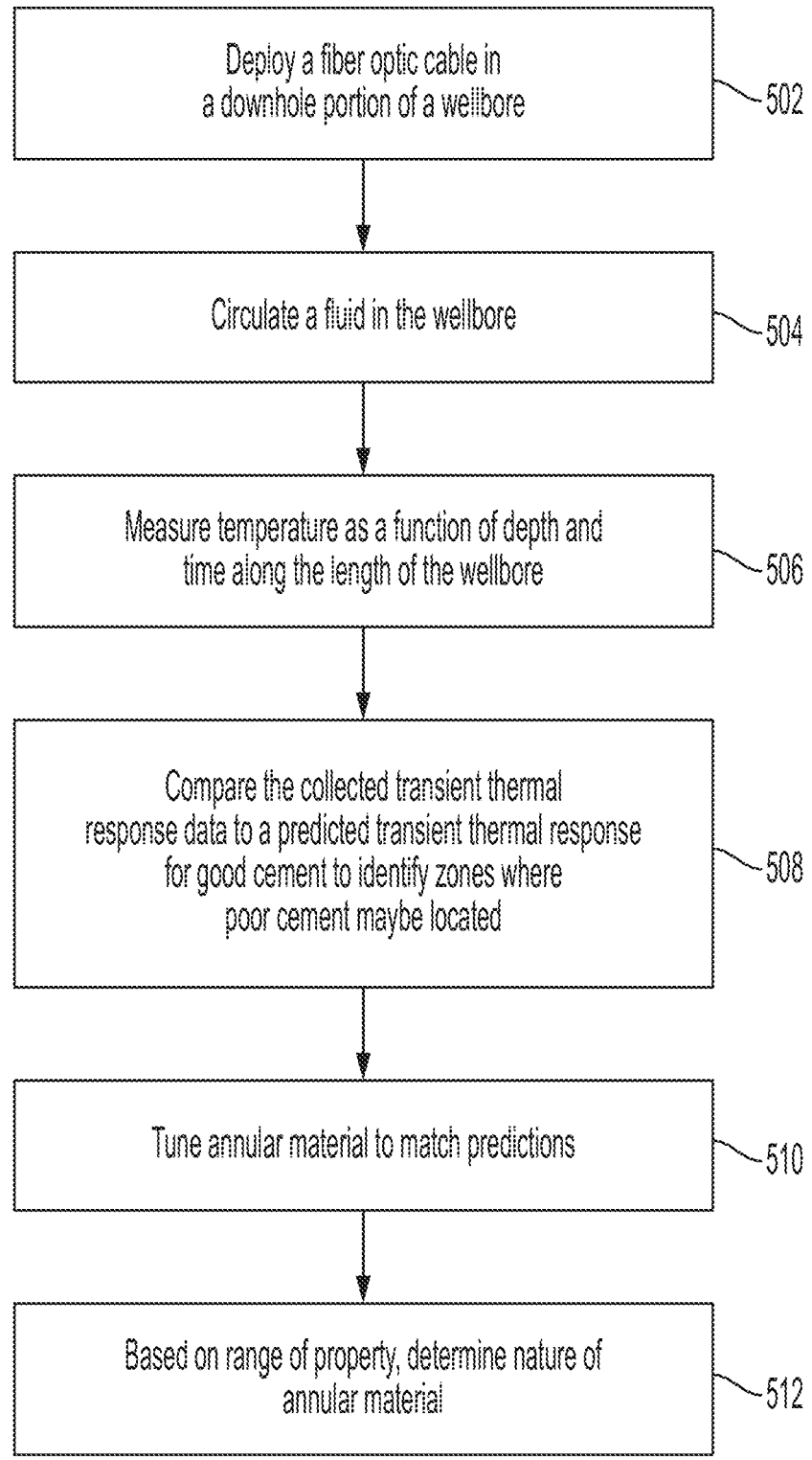
FIG. 5 is a flowchart of a process for evaluating an annular material in a wellbore using a wellbore assembly according to one example of the present disclosure.

FIG. 5 is a flowchart of a process for evaluating an annular material in a wellbore according to one example of the present disclosure.

In block 502, a fiber optic cable that can be coupled to a landing device can be deployed in a downhole portion of the wellbore. The fiber optic cable can be used to collect temperature data along the length of the fiber optic cable which correspond to temperature data along a length of the wellbore.

In block 504, a fluid can be circulated in the wellbore. The fluid can be a hot fluid or a cold fluid. As described above the temperature of the fluid can be selected to create a sufficient temperature gradient for monitoring the wellbore's return to thermal equilibrium over a period of time after the fluid is left static in the wellbore. The temperature of the fluid at the inlet can be for example approximately 50 to approximately 100 degrees Celsius higher or lower than the temperature at the surface of the wellbore, or any other suitable temperature differential may be used. After a pre-determined volume of fluid is circulated, for example but not limited to one to two hole volumes of fluid, the fluid may be left static in the wellbore.

In block 506, the fiber optic cable collects temperature data along the length of the wellbore over a period of time (i.e. collects transient thermal response data). The transient thermal response data can correspond in part to an annular material in the annulus of the casing string and the wellbore at the depth of the wellbore where the transient thermal response data is measured.

In block 508 the transient thermal response data collected by the fiber optic cable along the length of the wellbore (i.e. temperature data at points along the length of the fiber optic cable over a period of time) can be compared to a predicted transient thermal response along the length of the wellbore to identify zones or regions where the measured data deviates from the predicted response. In some embodiments, the predicted transient thermal response at various locations along the length of the wellbore can be determined using a mathematical model, for example a mathematical model for wellbore temperature modeling including conduction and convection heat transfer processes. The mathematical model may be a physics-based model that can be based in part on a convection process and a conduction process. The mathematical model may also provide for inputs related to the thermal properties of various materials in the well system, including but not limited to the casing string material, wellbore fluid, cement, formation or rock material, etc. Locations (or zones or regions) where the transient thermal response data collected by the fiber optic cable deviates, for example by at least a pre-determined amount, from the predicted transient thermal response data can correspond to locations where the annular material positioned within the annulus between the casing string and the wellbore may be weak, damaged, or otherwise poorly cemented.

In block 510, the thermal properties of the annular material described by the mathematical model can be tuned to match the measured transient thermal response data. In other words, the input values of the mathematical model, including but not limited to the thermal properties of the annular material, may be altered to tune the mathematical model to the measured transient thermal response data. The annular material may include a cement, a mud, a formation fluid, or any other material that may be present in the wellbore. The thermal properties may include a thermal conductivity. The thermal properties of the annular material of the location where the measured transient thermal response data deviates from the predicted transient thermal response data may thereby be determined at block 510.

In block 512, the thermal properties of the annular material that have been determined using the mathematical model may then can be used to determine a composition of the annular material in the wellbore. This can be done by performing a search on a lookup table to find materials that have thermal properties similar to the thermal properties identified in block 510 corresponding to the annular material in the zone where the measured data deviates from the predicted values. The lookup table can provide for thermal properties of various annular materials including but not limited to, cement, a mud, a formation fluid, or any other material that may be present in the wellbore.

Figure 6:
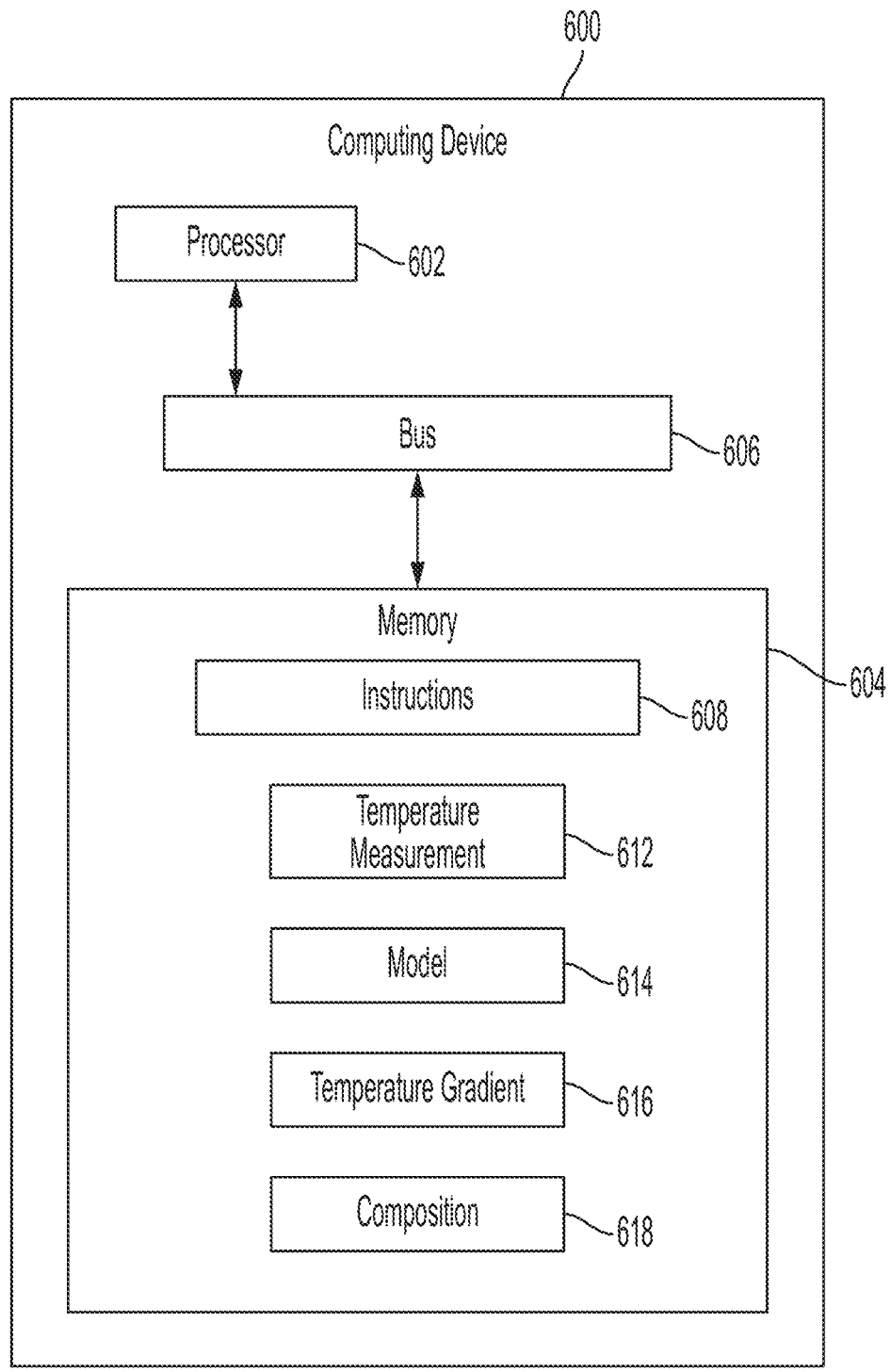
FIG. 6 is a schematic diagram of an exemplary computing device according to one example of the present disclosure.

FIG. 6 is a block diagram of a computing device 600 that can perform one or more steps of the methods and processes described above, for example in FIG. 5. The computing device 600 can include a processor 602, a bus 606, and a memory 604. In some examples, the components shown in FIG. 6 can be integrated into a single structure. For example, the components can be within a single housing with a single processing device. In other examples, the components shown in FIG. 6 can be distributed (e.g., in separate housings) and in electrical communication with each other using various processors. It is also possible for the components to be distributed in a cloud computing system or grid computing system.

The processor 602 can execute instructions 608 stored in the memory 604 to perform operations. In some examples, the instructions 608 may be executed by the processor 602 for causing the processor 602 to receive a temperature measurement 612 from a sensor device, for example a fiber optic cable. In some examples, a temperature gradient 616, which can be caused by a transient thermal response in an annular material, can be calculated using the temperature measurement 612. The instructions may include a model 614 for identifying regions of temperature deviation. The model may be a physics-based model or a mathematical model. The instructions may be used to determine a composition 618 of the annular material. The processor 602 can include one processing device or multiple processing devices. Non-limiting examples of the processor 602 include a field-programmable gate array ("FPGA"), an application-specific integrated circuit ("ASIC"), a processor, a microprocessor, etc.

The processor 602 can be communicatively coupled to the memory 604 via the bus 606. The memory 604 may include any type of memory device that retains stored information when powered off. Non-limiting examples of the memory 604 include electrically erasable and programmable read-only memory ("EEPROM"), flash memory, or any other type of non-volatile memory. In some examples, at least some of the memory 604 can include a non-transitory medium from which the processor 602 can read the instructions 608. A computer-readable medium can include electronic, optical, magnetic, or other storage devices capable of providing the processor 602 with computer-readable instructions or other program code. Non-limiting examples of a computer-readable medium include (but are not limited to) magnetic disk(s), memory chip(s), read-only memory (ROM), random-access memory ("RAM"), an ASIC, a configured processing device, optical storage, or any other medium from which a computer processing device can read instructions. The instructions can include processing device-specific instructions generated by a compiler or an interpreter from code written in any suitable computer-programming language, including, for example, C, C++, C#, etc.

Generally, the temperature sensors described above may include permanently installed sensors. The temperature sensors may also include fiber optic cables cemented in place in the annular space between the casing and formation. The fiber optic cables may be clamped to the outside of the casing during the deployment, and protected by centralizers and cross coupling clamps. Other types of permanent sensors may include surface and down-hole sensors. The fiber optic cables referenced herein may house one or several optical fibers and the optical fibers may be single mode fibers, multi mode fibers or a combination of single mode and multi mode optical fibers. The fiber optic sensing systems connected to the optical fibers may include Distributed Temperature Sensing (DTS) systems, Distributed Acoustic Sensing (DAS) Systems, Distributed Strain Sensing (DSS) Systems, quasi-distributed sensing systems where multiple single point sensors are distributed along an optical fiber/cable, or single point sensing systems where the sensors are located at the end of the cable. The fiber optic sensing systems may operate using various sensing principles including but not limited to amplitude based sensing systems like e.g. DTS systems based on Raman scattering, phase sensing based systems like e.g. DAS systems based on interferometric sensing using e.g. homodyne or heterodyne techniques where the system may sense phase or intensity changes due to constructive or destructive interference, strain sensing systems like DSS using dynamic strain measurements based on interferometric sensors or static strain sensing measurements using e.g. Brillouin scattering, quasi-distributed sensors based on e.g. Fiber Bragg Gratings (FBGs) where a wavelength shift is detected or multiple FBGs are used to form Fabry-Perot type interferometric sensors for phase or intensity based sensing, or single point fiber optic sensors based on Fabry-Perot or FBG or intensity based sensors.

In some aspects, methods for evaluating an annular material with transient temperature response data are provided according to one or more of the following examples:

As used below, any reference to a series of examples is to be understood as a reference to each of those examples disjunctively (e.g., "Examples 1-4" is to be understood as "Examples 1, 2, 3, or 4").

Example 1 is a method comprising: deploying a thermal sensor in a downhole portion of a wellbore; circulating a fluid in the wellbore for creating thermal gradients in a radial direction and an axial direction; collecting, from a thermal sensor, temperature data at a selected location along a length of the wellbore over a period of time; comparing, the temperature data collected by the thermal sensor at the selected location over the period of time, to predicted temperature data at the selected location over the period of time; determining that temperature data collected by the thermal sensor at the selected location of the period of time deviates from the predicted temperature data at the selected location over the period of time by a pre-determined amount.

Example 2 is the method of example 1, wherein the thermal sensor comprises a fiber optic cable.

Example 3 is the method of any of example(s) 1-2, further comprising: calculating the predicted temperature data at the selected location over the period of time using a mathematical model based at least in part on a selected annular material of the wellbore at the selected location.

Example 4 is the method of any of example(s) 1-3, wherein the model is a physics-based model that describes (i) a conduction process and (ii) a convention process.

Example 5 is the method of any of example(s) 1-4, wherein the physics-based model is further based on at least one of (i) thermal properties of a formation at the selected location, (ii) thermal properties of a casing string in the wellbore, or (iii) thermal properties of a wellbore fluid in the wellbore.

Example 6 is the method of any of example(s) 1-5, wherein the selected annular material of the wellbore is a cement in a properly cemented annulus.

Example 7 is the method of any of example(s) 1-6, further comprising: determining an annular material at the second location by determining an estimated thermal conductivity value of the annular material, and performing a search on a lookup table of thermal conductivities, and thereafter comparing the estimated thermal conductivity value of the annular material with a thermal conductivity value of a material contained in the lookup table.

Example 8 is the method of any of example(s) 1-7, further comprising: selecting a temperature of the fluid at an inlet in the wellbore; selecting a duration of circulating time of the fluid; and selecting a rate of the circulation of the fluid.

Example 9 is the method of any of example(s) 1-8, wherein the fiber optic cable is configured to couple to a landing device.

Example 10 is the method of any of example(s) 1-9 wherein the annular material is separated from the fiber optic cable by more than one casing string.

Example 11 is the method of any of example(s) 1-10, wherein the step of collecting, from the fiber optic cable, temperature data at a selected location along a length of the fiber optic cable over a period of time further comprises collecting temperature data at the selected location over about thirty minutes to about sixty minutes.

Example 12 is the method of any of example(s) 1-11, further comprising remediating cement at an annulus location corresponding to the selected location in response to determining temperature data collected by the fiber optic cable at the selected location of the period of time deviates from the predicted temperature data at the selected location over the period of time by the pre-determined amount.

Example 13 is the method of any of example(s) 1-12, wherein the step of remediating cement at an annulus location corresponding to the selected location in response to determining temperature data collected by the fiber optic cable at the selected location of the period of time deviates from the predicted temperature data at the selected location over the period of time by the pre-determined amount further comprising performing squeeze cementing at the annulus location.

Example 14 is a method comprising: deploying a fiber optic cable in a downhole portion of a wellbore; circulating a fluid in the wellbore for creating thermal gradients in a radial direction and an axial direction; collecting, from the fiber optic cable, temperature data at a first location along the fiber optic cable over a period of time; collecting, from the fiber optic cable, temperature data at a second location along the fiber optic cable over the period of time; and determining that the temperature data at the first location deviates from the temperature data at the second location over the period of time.

Example 15 is method of example 14, wherein the step of deploying a fiber optic cable in a downhole portion of a wellbore further comprises running the fiber optic cable through a tubing positioned within the wellbore.

Example 16 is the method of any of example(s) 14-15, wherein the fiber optic cable is configured to couple to a landing device.

Example 17 is the method of any of example(s) 14-16, wherein the annular material is separated from the fiber optic cable by more than one casing string.

Example 18 is the method of any of example(s) 14-17, further comprising determining an annular material at the second location by determining an estimated thermal conductivity value of the annular material, and performing a search on a lookup table of thermal conductivities, and thereafter comparing the estimated thermal conductivity value of the annular material with a thermal conductivity value of a material contained in the lookup table.

Example 19 is the method of any of example(s) 14-18 further comprising: remediating cement at an annulus location corresponding to the second location in response to determining the temperature data at the first location deviates from the temperature data at the second location over the period of time.

Example 20 is the method of any of example(s) 14-19, wherein the step of remediating cement at an annulus location corresponding to the second location in response to determining the temperature data at the first location deviates from the temperature data at the second location over the period of time further comprises performing squeeze cementing at the annulus location.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A method comprising:
   deploying a thermal sensor in a downhole portion of a wellbore;
   circulating a fluid in the wellbore for creating thermal gradients in a radial direction and an axial direction;
   collecting, from the thermal sensor, temperature data at a selected location along a length of the wellbore over a period of time in which the fluid is left static in the wellbore as the wellbore is returning to a thermal equilibrium;
   comparing, the temperature data collected by the thermal sensor at the selected location over the period of time, to predicted temperature data at the selected location over the period of time; and
   determining that temperature data collected by the thermal sensor at the selected location over the period of time deviates from the predicted temperature data at the selected location over the period of time by a pre-determined amount.

2. The method of claim 1, wherein the thermal sensor comprises a fiber optic cable.

3. The method of claim 2, further comprising:
   calculating the predicted temperature data at the selected location over the period of time using a mathematical model based at least in part on a selected annular material of the wellbore at the selected location.

4. The method of claim 3, wherein the mathematical model is a physics-based model that describes (i) a conduction process and (ii) a convection process.

5. The method of claim 4, wherein the physics-based model is further based on at least one of (i) thermal properties of a formation at the selected location, (ii) thermal properties of a casing string in the wellbore, or (iii) thermal properties of a wellbore fluid in the wellbore.

6. The method of claim 3, wherein the selected annular material of the wellbore is a cement in a properly cemented annulus.

7. The method of claim 2, further comprising:
determining an annular material at the selected location by:
determining an estimated thermal conductivity value of the annular material;
performing a search on a lookup table of thermal conductivities; and comparing the estimated thermal conductivity value of the annular material with a thermal conductivity value of a material contained in the lookup table.

8. The method of claim 7 wherein the annular material is separated from the fiber optic cable by more than one casing string.

9. The method of claim 2, wherein the fiber optic cable is configured to couple to a landing device.

10. The method of claim 2, wherein the step of collecting, from the fiber optic cable, temperature data at a selected location along a length of the fiber optic cable over a period of time further comprises collecting temperature data at the selected location over about thirty minutes to about sixty minutes.

11. The method of claim 2, further comprising remediating cement at an annulus location corresponding to the selected location in response to determining temperature data collected by the fiber optic cable at the selected location of the period of time deviates from the predicted temperature data at the selected location over the period of time by the pre-determined amount.

12. The method of claim 11, wherein the step of remediating cement at an annulus location corresponding to the selected location in response to determining temperature data collected by the fiber optic cable at the selected location of the period of time deviates from the predicted temperature data at the selected location over the period of time by the pre-determined amount further comprising performing squeeze cementing at the annulus location.

13. The method of claim 1, further comprising:
selecting a temperature of the fluid at an inlet in the wellbore;
selecting a duration of circulating time of the fluid; and
selecting a rate of the circulation of the fluid.

14. A method comprising:
deploying a fiber optic cable in a downhole portion of a wellbore;
circulating a fluid in the wellbore for creating thermal gradients in a radial direction and an axial direction;
collecting, from the fiber optic cable, temperature data at a first location along the fiber optic cable over a period of time;
collecting, from the fiber optic cable, temperature data at a second location along the fiber optic cable over the period of time in which the fluid is left static in the wellbore and is returning to a thermal equilibrium; and
determining that the temperature data at the first location deviates from the temperature data at the second location over the period of time.

15. The method of claim 14, wherein the step of deploying a fiber optic cable in a downhole portion of a wellbore further comprises running the fiber optic cable through a tubing positioned within the wellbore.

16. The method of claim 14, wherein the fiber optic cable is configured to couple to a landing device.

17. The method of claim 14, further comprising:
determining an annular material at the second location by:
determining an estimated thermal conductivity value of the annular material;
performing a search on a lookup table of thermal conductivities; and comparing the estimated thermal conductivity value of the annular material with a thermal conductivity value of a material contained in the lookup table.

18. The method of claim 17 wherein the annular material is separated from the fiber optic cable by more than one casing string.

19. The method of claim 14 further comprising: remediating cement at an annulus location corresponding to the second location in response to determining the temperature data at the first location deviates from the temperature data at the second location over the period of time.

20. The method of claim 19, wherein the step of remediating cement at an annulus location corresponding to the second location in response to determining the temperature data at the first location deviates from the temperature data at the second location over the period of time further comprises performing squeeze cementing at the annulus location.

* * * * *